United States Patent
Krupnik

(10) Patent No.: US 9,412,054 B1
(45) Date of Patent: Aug. 9, 2016

(54) DEVICE AND METHOD FOR DETERMINING A SIZE OF IN-VIVO OBJECTS

(75) Inventor: Hagai Krupnik, Nofit (IL)

(73) Assignee: GIVEN IMAGING LTD., Yoqneam (IL)

( * ) Notice: Subject to any disclaimer, the term of this patent is extended or adjusted under 35 U.S.C. 154(b) by 465 days.

(21) Appl. No.: 13/237,117

(22) Filed: Sep. 20, 2011

Related U.S. Application Data

(60) Provisional application No. 61/384,483, filed on Sep. 20, 2010.

(51) Int. Cl.
*G06K 9/00* (2006.01)
*G06K 9/80* (2006.01)
*G06K 9/42* (2006.01)

(52) U.S. Cl.
CPC ... *G06K 9/80* (2013.01); *G06K 9/42* (2013.01)

(58) Field of Classification Search
None
See application file for complete search history.

(56) References Cited

U.S. PATENT DOCUMENTS

| | | | |
|---|---|---|---|
| 5,372,502 A * | 12/1994 | Massen et al. | 433/215 |
| 5,604,531 A | 2/1997 | Iddan et al. | |
| 6,297,488 B1 * | 10/2001 | Beraldin et al. | 250/201.2 |
| 7,009,634 B2 | 3/2006 | Iddan et al. | |
| 7,995,798 B2 * | 8/2011 | Krupnik et al. | 382/106 |
| 8,308,633 B2 * | 11/2012 | Banju | 600/118 |
| 8,547,642 B2 * | 10/2013 | Chen et al. | 359/641 |
| 8,655,042 B2 * | 2/2014 | Florent | 382/132 |
| 8,676,013 B2 * | 3/2014 | Bouma et al. | G02B 6/02042 385/115 |
| 8,792,691 B1 * | 7/2014 | Rozenfeld | G06T 7/2033 382/128 |
| 2005/0240077 A1 * | 10/2005 | Rovegno | 600/108 |
| 2006/0217593 A1 * | 9/2006 | Gilad et al. | A61B 1/0005 600/160 |
| 2007/0249900 A1 * | 10/2007 | Wilson et al. | A61B 1/00036 600/116 |
| 2007/0255098 A1 * | 11/2007 | Wang | A61B 1/041 600/109 |
| 2008/0039692 A1 * | 2/2008 | Hirakawa | 600/160 |
| 2009/0016491 A1 * | 1/2009 | Li | 378/98.5 |
| 2009/0097725 A1 * | 4/2009 | Krupnik et al. | 382/128 |
| 2009/0318760 A1 * | 12/2009 | Pascal et al. | 600/117 |
| 2010/0106423 A1 * | 4/2010 | Graf et al. | G06K 9/6228 702/19 |
| 2010/0272318 A1 * | 10/2010 | Cabiri et al. | 382/106 |
| 2011/0242301 A1 * | 10/2011 | Morita | A61B 1/00009 348/65 |

OTHER PUBLICATIONS

Tankus et al., "Reconstruction of Medical Images by Perspective Shape-from-Shading", Tel-Aviv University Press, Israel, 2004, pp. 1-4.
Forster et al., "Towards 3D Reconstruction of Endoscope Images Using Shape from Shading", IEEE 2000, pp. 90-96.
Okatani et al., "Shape Reconstruction from an Endoscope Image by Shape from Shading Technique for a Point Light Source at the Projection Center", Computer Vision and Image Understanding, Elsevier, vol. 66, No. 2, May 1997, pp. 119-131.

* cited by examiner

*Primary Examiner* — Nancy Bitar
(74) *Attorney, Agent, or Firm* — Pearl Cohen Zedek Latzer Baratz LLP

(57) ABSTRACT

A system and method for estimating a size of an object in an image is provided. A tissue model may be provided. Points in an image may be selected. A distance or estimated distance of the points from an imaging device may be determined based on the tissue model. A geometrical relation associating the point, distances and an object may be derived. A size parameter of the object may be calculated based on the geometrical relation. Other embodiments are described and claimed.

23 Claims, 8 Drawing Sheets

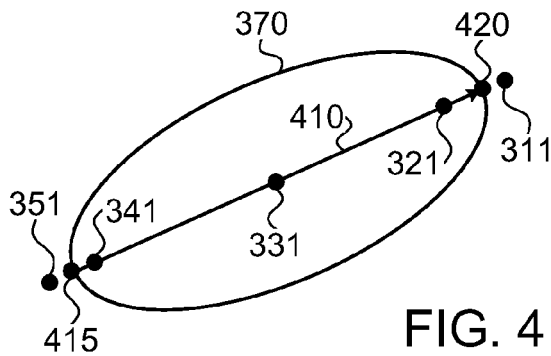

FIG. 4

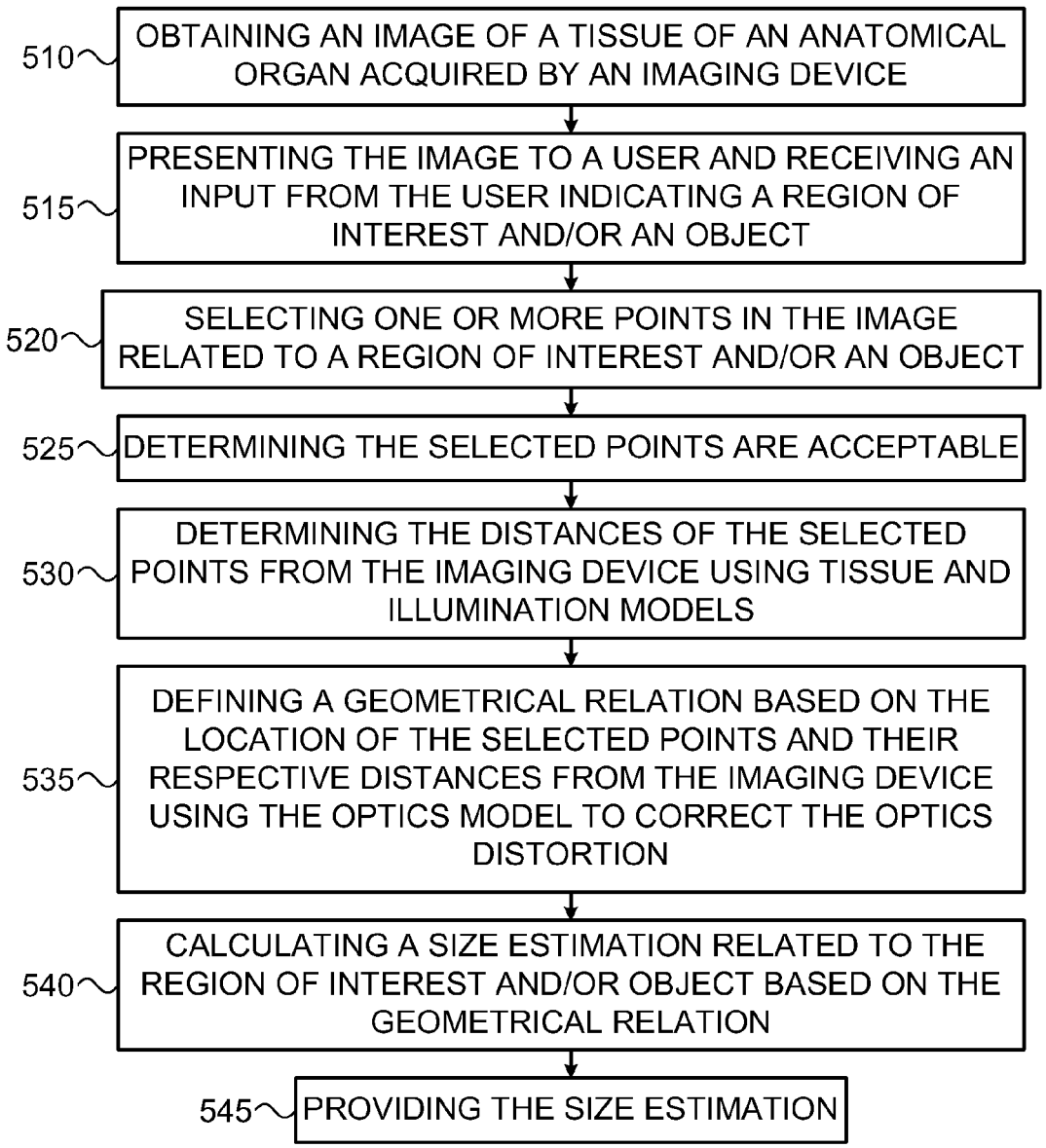

510 — OBTAINING AN IMAGE OF A TISSUE OF AN ANATOMICAL ORGAN ACQUIRED BY AN IMAGING DEVICE

515 — PRESENTING THE IMAGE TO A USER AND RECEIVING AN INPUT FROM THE USER INDICATING A REGION OF INTEREST AND/OR AN OBJECT

520 — SELECTING ONE OR MORE POINTS IN THE IMAGE RELATED TO A REGION OF INTEREST AND/OR AN OBJECT

525 — DETERMINING THE SELECTED POINTS ARE ACCEPTABLE

530 — DETERMINING THE DISTANCES OF THE SELECTED POINTS FROM THE IMAGING DEVICE USING TISSUE AND ILLUMINATION MODELS

535 — DEFINING A GEOMETRICAL RELATION BASED ON THE LOCATION OF THE SELECTED POINTS AND THEIR RESPECTIVE DISTANCES FROM THE IMAGING DEVICE USING THE OPTICS MODEL TO CORRECT THE OPTICS DISTORTION

540 — CALCULATING A SIZE ESTIMATION RELATED TO THE REGION OF INTEREST AND/OR OBJECT BASED ON THE GEOMETRICAL RELATION

545 — PROVIDING THE SIZE ESTIMATION

FIG. 5

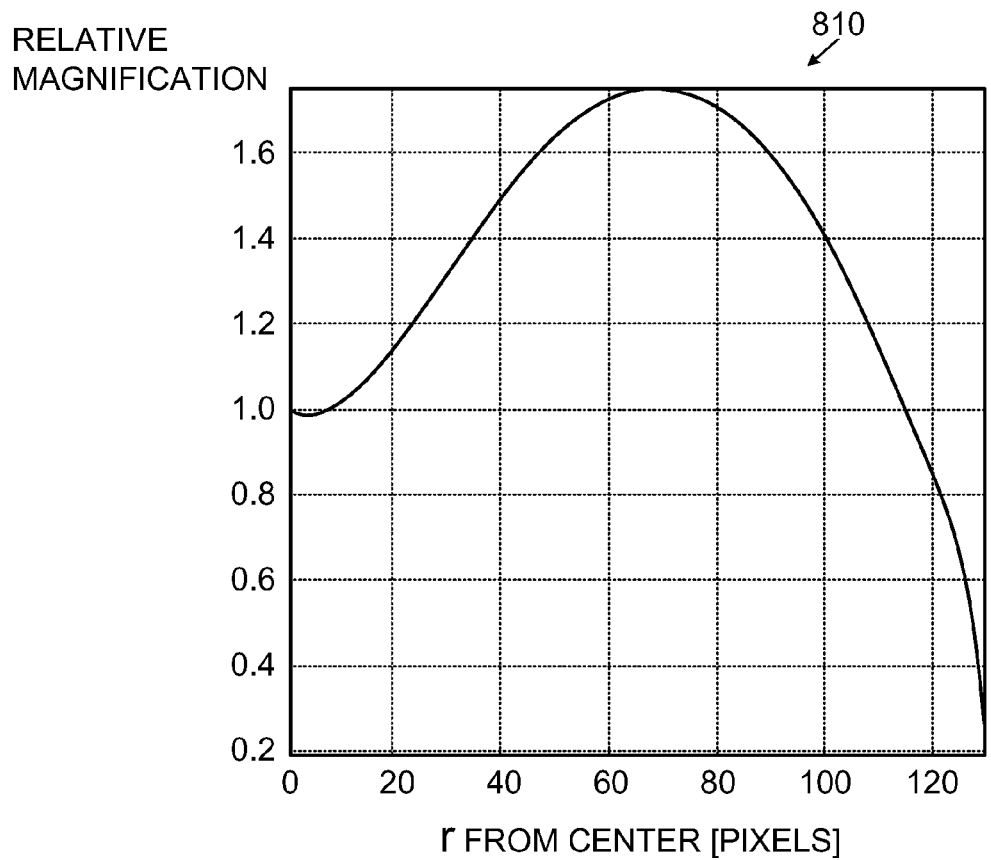
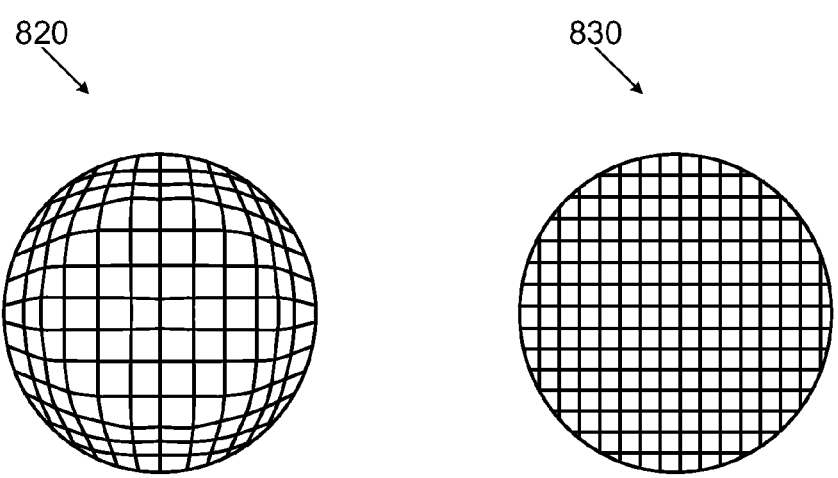
FIG. 8

DEVICE AND METHOD FOR DETERMINING A SIZE OF IN-VIVO OBJECTS

REFERENCE TO RELATED APPLICATIONS

This patent application claims priority from U.S. provisional patent application Ser. No. 61/384,483 filed Sep. 20, 2010, which is incorporated herein by reference in its entirety.

FIELD OF THE INVENTION

The present invention relates to the field of estimating a geometrical parameter of objects in an image. More specifically, the present invention relates to estimating or determining a size of objects in an image. In particular, the present invention relates to images obtained by an in-vivo device, and estimating parameters of in-vivo objects, regions or tissues, e.g. a size of an in-vivo object or tissue.

BACKGROUND OF THE INVENTION

Known devices may be helpful in providing in-vivo sensing, for example, using imaging techniques, systems and/or methods. One of the uses for such devices may be in detecting and/or identifying objects or tissues that may indicate in-vivo pathologies. Autonomous in-vivo sensing devices, e.g., swallowable or ingestible capsules or other devices may move through a body lumen, sensing, monitoring or otherwise obtaining data as they move along body lumens. Such autonomous in-vivo sensing devices may include, for example, an imager for obtaining images of a body cavity or lumen, such as the gastrointestinal (GI) tract. Such autonomous in-vivo sensing devices may include an optical system, a light source, a controller and optionally a transmitter and an antenna. Some of these devices use a wireless connection to transmit image data.

Different methods for estimating the size of objects imaged in a body lumen exist. For example, an in-vivo device may emit a laser beam and may further acquire an image of a spot on a tissue created by such beam as well as surrounding tissues or region. A distance of the spot from the in-vivo device may be calculated, e.g., based on the location of the spot in an image. Various parameters, coefficients or other information related to a color or other optical aspects of nearby tissue (that may be assumed to be in the same and known distance of the laser beam spot) may be calculated and applied to other regions, objects or tissues in the image in order to calculate a distance of such other regions, objects or tissues from the in-vivo device.

SUMMARY OF THE INVENTION

Embodiments of the present invention may enable the estimation or determination of one or more parameters, e.g., size, volume, ratio or a dimension of objects or regions seen in in-vivo images obtained from within body lumens or cavities, such as the gastrointestinal (GI) tract. According to an embodiment of the invention, predefined calculations, processing and analysis may be performed on images obtained from within body lumens in order to present to an observer parameters such as a size of an object seen in an image.

According to embodiments of the invention there may be provided, in an in-vivo imaging device, an imaging system and an illumination source to provide illumination for the imaging system. In some embodiments, acquired images may be stored on a storage device installed on the device. Additionally or alternatively, an in-vivo device may be equipped with a transmitter and/or receiver and may be configured to communicate with a remote computing device or system. In some embodiments, acquired images may be transmitted by an in-vivo device to a remote computer or system or to an image receiver. A workstation or other suitable computing device may receive images obtained by an in-vivo imaging device and may estimate or determine a size of objects or regions in images as described herein. An in-vivo device may be equipped with any suitable processor, controller or other computing system that may perform any applicable tasks such as examining, analyzing or otherwise processing images or performing tasks related to controlling, coordinating or otherwise managing operation of any component in an in-vivo device. In some embodiments, a computing system installed on an in-vivo device may perform an estimation or determination of a size or other parameter of an in-vivo object by processing images as described herein.

According to embodiments of the invention, there may be provided a system and method for estimating or determining a distance, a size or other parameters related to objects or regions in a body lumen. The method according to one embodiment of the invention may include generating and/or obtaining a tissue model that may be associated with, or based on, various optical parameters, imaging parameters or other relevant parameters. For example, parameters related to an intensity and/or color of light reflected or emitted from tissues may be used to design, set, configure or determine in a tissue model. Accordingly, a tissue model may be based on such determined or known parameters. A model may enable mapping or otherwise relating one or more parameters to a geometrical parameter. For example, as determined by a tissue model, a set of specific values associated with a pixel in a digital image may be mapped to a distance or estimated distance of an object associated with the pixel, from the imaging device used for acquiring the digital image. A suitable tissue model may be associated with, or related to an image of an inner region of a human or mammal, and may be obtained by an in-vivo device described herein.

In some embodiments, based on a tissue model, an optical model and an illumination model, and/or other information such as parameters of the imaging system and based on a color and/or intensity of pixels in an image, the distance or estimated distance of objects or regions represented by, or associated with such pixels from the imager used for obtaining the digital image may be calculated. For example, a chart, graph, function or equation may correlate a specific set of values, levels or other aspects of a specific color, intensity or a specific combination of such and other parameters with a distance. As described herein, provided with a distance of an object in an image, a size of the object may be determined. In some embodiments, a tissue model may include an optical model and/or an illumination model.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which:

FIG. 4 shows exemplary points selected in an image according to embodiments of the present invention;

FIG. 5 shows a flow-chart illustrating a method in accordance with embodiments of the invention;

FIG. 8 is a graph modeling an optical parameter according to embodiments of the present invention.

Figure 1A:
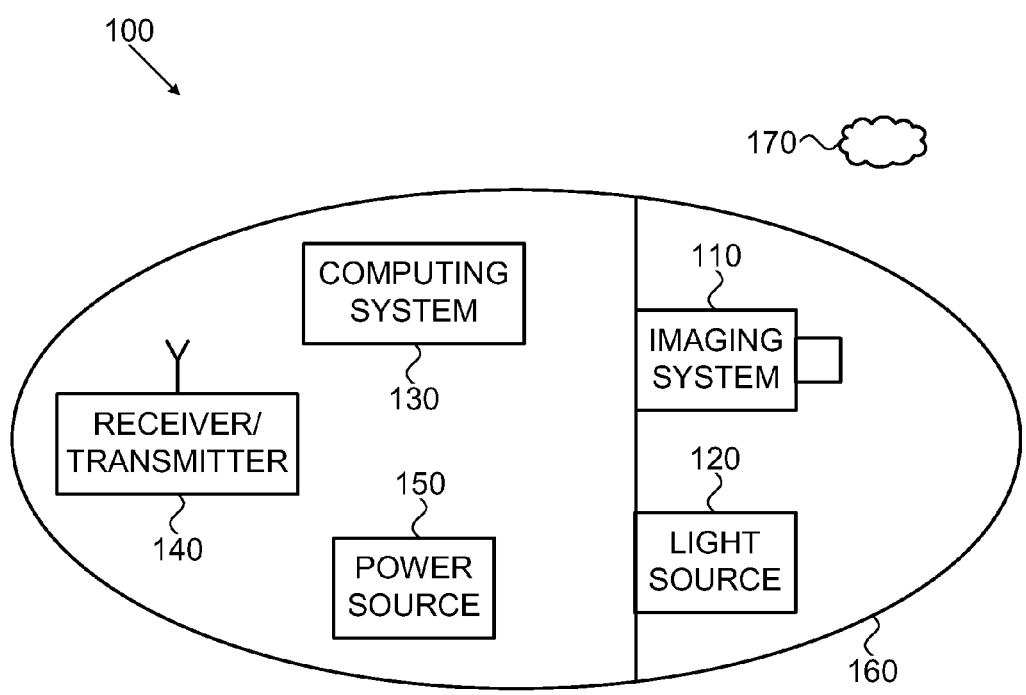
FIG. 1A shows a schematic diagram of an in-vivo imaging device according to embodiments of the invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed at the same point in time.

Embodiments of the system and method of the present invention may be used in conjunction with an imaging system or device capable of obtaining images of in-vivo objects. More specifically, in some embodiments, any imaging device or system that may be installed in an in-vivo device as described herein may be used. However, it will be understood that embodiments of the invention are not limited by the type, nature or other relevant aspects of the imaging system, device or unit used.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in U.S. Pat. No. 7,009,634 and/or in U.S. Pat. No. 5,604,531, each of which are assigned to the common assignee of the present invention and each of which are hereby incorporated by reference in their entirety. Of course, devices and systems as described herein may have other configurations and other sets of components.

According to one embodiment, an in-vivo imaging device may collect a series of still images as it traverses the GI tract. The images may be later presented as, for example, a stream or sequence of images or a moving image of the traverse of the GI tract. An in-vivo imaging device or system may collect a large volume of data, as the in-vivo imaging device may take several hours to traverse the GI tract. The in-vivo imaging device may record images at a rate of, for example, four to forty images per second (other rates, such as two frames per second, may be used). The in-vivo imaging device may have a fixed or variable frame capture and/or transmission rate. When the in-vivo imaging device has a variable or adaptive frame rate (AFR), the in-vivo imaging device may switch back and forth between frame rates, for example, based on parameters, such as an imaging device speed, estimated location, similarity between consecutive images, or other criteria. A total of thousands of images, for example, 50,000 images, may be recorded. The image recordation rate, the frame capture rate, the total number of images captured, the total number of images selected if the moving image is edited, and the view time of the moving image, may each be fixed or varied.

The image data recorded and transmitted by the in-vivo imaging device may be digital color image data, although in alternate embodiments other image formats may be used. In one example, each frame of image data may include 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in a data processor storage unit. The stored data may include one or more pixel properties, including color, intensity and brightness.

While information gathering, storage and processing are described to be performed by certain units, the system and method of the present invention may be practiced with alternate configurations. For example, the components gathering image information need not be contained in an imaging device, but may be contained in any other vehicle suitable for traversing a lumen in a human body, such as an endoscope, stent, catheter, needle, etc. A data processor storage unit may store a series of images recorded by an in-vivo imaging device. The images the in-vivo imaging device records as it moves through a patient's GI tract may be combined consecutively to form a moving image stream or video.

According to some embodiments, a distance from an imaging device and/or a size of an object may be determined or estimated by obtaining a tissue model designed to provide at least a mapping of at least one imaging parameter to at least one distance parameter, obtaining, by an imaging system, a digital image of the object, selecting at least one pixel in the digital image, wherein such at least one pixel is associated with the object, e.g., represents at least part of the object in the digital image and calculating, based on the tissue model and data associated with the pixel, a distance parameter related to a distance of the object from the imaging system.

Embodiments of the invention may calculate a size of an object by selecting at least two pixels in the digital image which includes the object, wherein the at least two pixels are associated with the object, e.g., represent at least part of the object in the digital image, and calculating the size of the object by relating a sum related to the pixels to an imaging parameter related to the imaging system. For example, given the distance or estimated distance, a ratio of number of pixels to area may be determined by an imaging parameter of the imaging device, e.g., a pixel resolution of the imaging device as known in the art.

Embodiments of the invention may calculate a size of an object by selecting at least two pixels in a digital image, wherein the at least two pixels are associated with respective at least two locations in a space captured by said digital image. For example, the pixels may represent at least part of tissues in the locations. Embodiments of the invention may further determine, based on a tissue model and data associated with the selected pixels, at least two distance parameters respectively related to a distance of the at least two locations from an imaging system. For example, the distance of two locations near an object may be calculated. A geometrical relation of the at least two locations and their respective distance from the imaging system to an object may be determined and, a size or other parameter of the object may be calculated based on the geometrical relation.

An imaging parameter or imaging information as referred to herein may be any information related to or associated with an image. For example, imaging parameters, values or information may be associated with, and obtained from pixels in a digital image as known in the art. Accordingly, it will be understood that any information that may be associated with pixels of a digital image or other imaging representations, e.g., a hue, intensity, color, saturation and the like may be obtained, analyzed and/or processed as described herein. Likewise, an image as referred to herein may typically (but not necessarily) be a digital image or representation of a space as captured by an imaging device. Embodiments of the invention may base a processing of an image on specific information, parameters or other aspects of the imaging device, e.g., a relation of pixels to size may be determined using a known resolution parameter of the imaging device used for acquiring or digitizing an image. Accordingly, parameters related to the imaging device may likewise be referred to herein as imaging parameters.

For example, given the distance of an object in an image (e.g., the distance of the object from the imaging system at the time the image was acquired), a relation of the number of pixels associated with the object (e.g., the number of pixels enclosed by an edge of the object) with the size of the object may be determined based on known parameters of the imaging system.

Reference is now made to FIG. 1A, which shows a schematic diagram of an in-vivo imaging device 100 according to one embodiment of the present invention. As shown, in-vivo imaging device 100 may include an imaging system 110, a light source 120, a computing device 130, a receiver transmitter 140, a power source 150 (e.g., an internal battery or a wireless receiving system) and a viewing window or dome 160. In some embodiments, in-vivo imaging device 100 may be, for example, a swallowable capsule capable of capturing images and/or obtain other data. More specifically, in-vivo device 100 may be configured, designed or otherwise enabled to independently obtain images and further configured to perform at least one of: processing, storing images and other information, communicating images to a remote computing or communication device and/or provide information, data or parameters related to obtained and/or processed images. For example, while inside a body of a human or other living creature, in-vivo device 100 may obtain images of tissues, objects or its surroundings, store, process and/or communicate such obtained images as well as possibly calculate, compute, determine and provide various indications, alarms, results or measurements.

In some embodiments, in-vivo device 100 may be in the shape of a capsule as shown in FIG. 1A, including for example a viewing window or dome 160. Viewing window 160 may be convex or substantially convex and smooth, and may project outward from the main body and/or housing of device 100. Viewing window 160 may be designed to provide a suitable field of view (FOV) for imaging system 110 and/or to enable light from light source 120 to reach objects outside device 100, e.g., object 170 as shown. Other shapes may be used, and the device need not be swallowable or a capsule. For example, device 100 may be implanted, inserted or otherwise located in any applicable location.

Imaging system 110 may be any suitable imaging system. For example, imaging system 110 may include any number of lenses or mirrors, support assemblies that may be used to direct imaging system 110 at a specific direction or angle and/or an embedded control module. Imaging system 110 may comprise a complementary metal oxide semiconductor (CMOS) imaging camera. As known in the art, a CMOS imager is typically an ultra low power imager and is provided in chip scale packaging (CSP). Other types of CMOS or other imagers may be used, e.g., a CCD imager. A 320×320 pixel imager may be included in imaging system 110, e.g., one having pixel size between 5 to 6 microns. According to some embodiments pixels may be each fitted with a micro lens.

Light source 120 may be any suitable light or energy source capable of producing, e.g., periodically or continually, light or other form of energy that may interact with objects outside device 100, e.g., object 170 shown in FIG. 1A. For example, light emitted periodically or continually by light source 120 may be reflected from such objects and captured by imaging system 110. For example, light source 120 may be a set of light emitting diodes (LEDs), organic LEDs (OLEDs), or other suitable light sources, may provide light to illuminate objects thus enable acquiring images as known in the art. In other embodiments, other forms of energy or types of light may be produced by light source 120, e.g., any form light or energy that imaging system 110 is capable of acquiring.

Computing system 130 may be any suitable article, processor, chip, controller or suitable computing device suitable for processing images as described herein as well as controlling, coordinating or otherwise manage components in device 100. For example, computing system 130 may perform one or more of: causing imaging system 110 to acquire an image, process the image, cause such image to be stored on a local storage (not shown) in device 100, cause such image to be communicated to a remote device, e.g., by controlling transmitter/receiver 140 and the like. In some embodiments, computing system 130 need not be a separate component; for example, parts of computing system 130 may be integral to, or embedded in, imaging system 110 or receiver transmitter 140. It will be understood that any functionality of computing system 130 may be distributed to any applicable or suitable component of device 100.

Transmitter/receiver 140 may transmit and/or receive images and/or other (e.g., non-image) information to/from a remote device. For example, a computer configured to wirelessly communicate with device 100 may be placed near a patient and may wirelessly communicate with device 100. Transmitter/receiver 140 may be an ultra low power radio frequency (RF) transmitter with high bandwidth input, possibly provided in chip scale packaging, may be combined with a processing chip or circuit and may transmit and/or receive information via an antenna as shown. Device 100 may include a power source 150, such as one or more batteries. For example, power source 150 may include silver oxide batteries, lithium batteries, or other electrochemical cells having a high energy density, or the like. Other power sources may be used. Other components, modules or units may be used. For example, power source 150 may be capable of receiving power from an external power source transmitting power to the device 100.

Embodiments of device 100 may typically be autonomous and/or self-contained. For example, the device may be a capsule or other unit where components are substantially contained within a container or shell, and where the device does not require any wires or cables to, for example, receive power, obtain, store or transmit information etc. Device 100 may communicate with an external computing or communication system that may receive, process, store, communicate and display images or other data or information received from device 100. Such remote system or device may further be used to control or otherwise interact with device 100. Accordingly, it will be understood that processing of digital images and determining parameters related to distance and/or size as described herein may be performed by a remote computing system configured to receive images acquired by in-vivo device 100.

In some embodiments, some or all of the processing of images as described herein may be performed by device 100, e.g., using computing system 130. In other embodiments, device 100 may perform some of the processing described herein and another computing system, e.g., a remote system may perform other processing or tasks. In yet other embodiments, device 100 may only obtain images, perform limited or no processing of such acquired images and send the images to a remote computing device or system which may perform processing, analyzing and determining of various parameters based on received images, e.g., such remote system may display images to a physician, receive a selection from the physician and, determining a size of an object shown in an image based on the physician's selection.

A storage unit may be worn on the patient's body and may communicate with device 100 to record acquired images. The storage unit may subsequently communicate with a computer, e.g., a workstation or server that may receive such stored images and further process them as described herein, e.g., compute and/or calculate size of objects shown in such images.

Figure 1B:
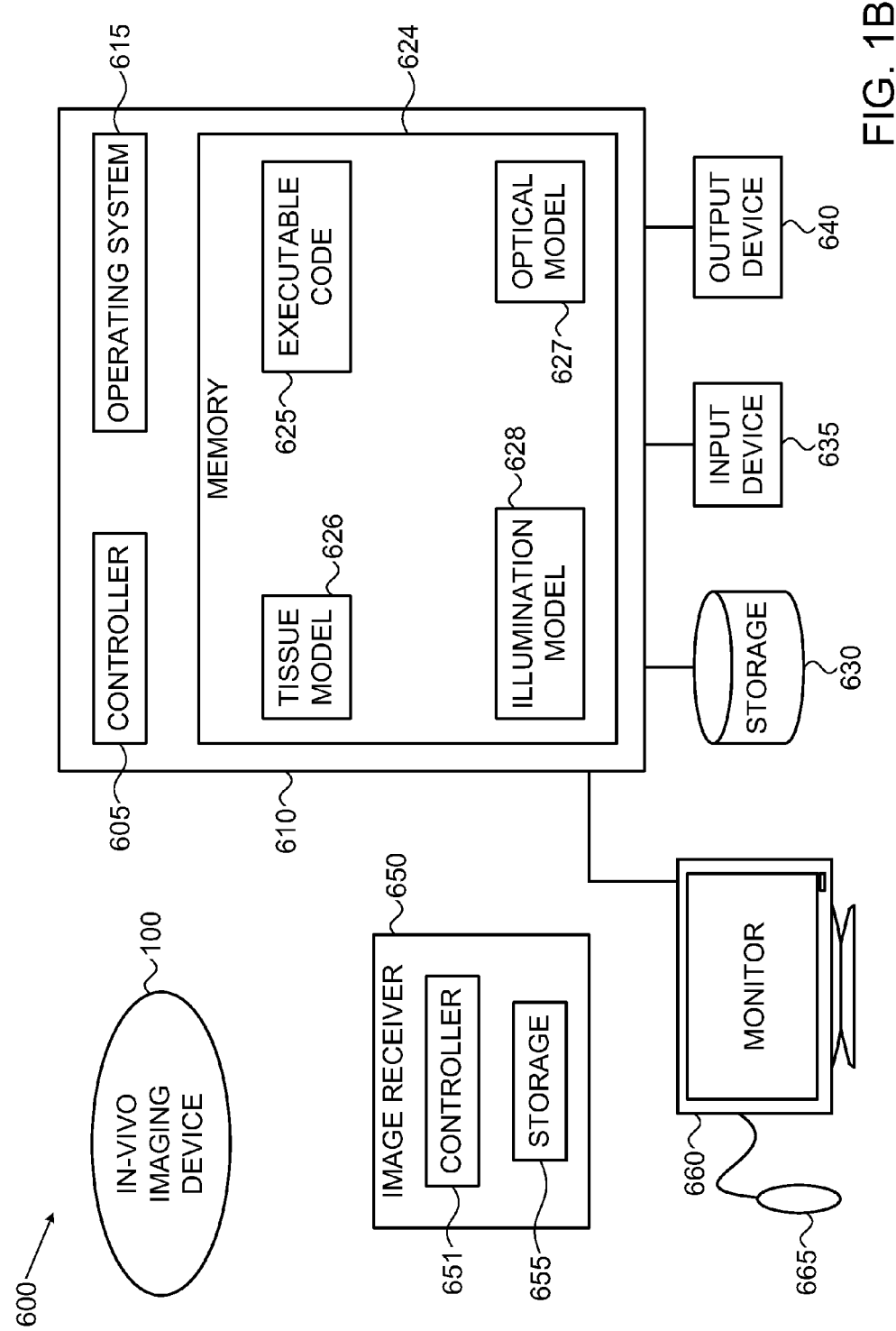
FIG. 1B shows a schematic illustration of an in-vivo imaging system, according to an embodiment of the present invention.

Reference is now made to FIG. 1B that shows a schematic illustration of an in-vivo imaging system 600, according to an embodiment of the present invention. According to some embodiments, system 600 may include an in-vivo imaging device, for example, an in-vivo imaging device 100 as described herein. As described herein, in-vivo imaging device 100 may be a swallowable in-vivo imaging device, but other types of devices or suitable implementations may be used. According to one embodiment, in-vivo imaging device 100 may communicate with an external receiving and display system to provide display of data, control, or other functions. System 600 may include an image receiver 650 including processor or controller 651 and a storage unit 655. For the sake of simplicity, various components that may be installed or included in image receiver 650 are not shown. For example, image receiver 650 may include output and input components or devices that may be similar to input device 635 and an output device 640 and/or an operating system similar to operating system 615, memory similar to memory 624, etc. It will be understood that image receiver 650 may be any suitable computing device and may perform any operations related to estimating or determining a distance, size or other dimensions of an object shown in an image as described herein.

Image receiver 650, which may include an antenna or antenna array, an image receiver storage unit 655 and a data processor or controller may be a small device that may be carried by a patient. For example, an (e.g. ambulatory) patient may wear image receiver 650 on a belt or wrist. Image receiver 650 may communicate, e.g., wirelessly, with in-vivo device 100, receive, from in-vivo device 100, images and store received images on storage 655. Accordingly, image receiver 650 may be attached to or worn on a patient or subject and may collect images obtained by in-vivo imaging device 100 over a relatively long period of time. Image receiver 650 may be configured to communicate, wirelessly or otherwise, with computing system 610 and transfer images and/or other information to computing system 610. For example, images and/or other information received from in-vivo imaging device 100 may be stored on storage 655 and may be transferred from storage 655 to computing system 610, e.g., using wireless communication, a universal serial bus (USB) connection or any suitable mechanism or communication method.

Computing system 610 may analyze, process or otherwise manipulate or handle any applicable images acquired by any suitable imaging device in any applicable environment and/or of any applicable objects. Likewise, according to embodiments of the invention, computing system 610 may compute or derive size estimations of objects or regions in any applicable images. In a particular embodiment, computing system 610 may receive images from in-vivo device 100 or image recorder 650 and may produce an estimation of a size of objects in such images. In some embodiments, in-vivo imaging device 100 may perform tasks as described herein with reference to computing system 610. For example, in-vivo imaging device 100 may include some components of computing system 610 as well as possibly, additional components. Accordingly, various operations and tasks that may be performed by computing system 610 may be performed by in-vivo imaging device 100, e.g., by computing system 130 or, in other embodiments, by image receiver 650. In some embodiments, processing of images performed in order to estimate a distance, size or other dimension of an object may be distributed. For example, a first part of the processing may be performed by computing system 130 in in-vivo device 100 and a second part may be performed by system 610. For example, an image may be modified by computing system 130 in in-vivo device 100 according to an illumination model, e.g., values associated with pixels may be altered based on an illumination or optical model which may be device specific. Such pre-processed image may then be communicated to system 610 that may perform a distance, size or other dimension estimation.

Computing system 610 may include a controller 605 that may be, for example, a central processing unit processor (CPU), a chip or any suitable computing or computational device, an operating system 615, a memory 624, a storage 630, an input device 635 and an output device 640. Operating system 615 may be or may include any code segment designed and/or configured to perform tasks involving coordination, scheduling, arbitration, supervising, controlling or otherwise managing operation of computing system 610, for example, scheduling execution of programs loaded into memory 624. In some embodiments, operating system 615 may be a commercial operating system. Memory 620 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 624 may be or may include a plurality of, possibly different memory units.

Executable code 625 may be any executable code, e.g., an application, a program, a process, task or script. Executable code 625 may be executed by controller 605 possibly under control of operating system 615. For example, executable code 625 may be an application designed to analyze an image and determine the distance of objects in such image from the imaging device used for acquiring the image. Storage 630 may be or may include, for example, a hard disk drive, a floppy disk drive, a Compact Disk (CD) drive, a CD-Recordable (CD-R) drive, a universal serial bus (USB) device or other suitable removable and/or fixed storage unit.

Input devices 635 may be or may include a mouse, a keyboard, a touch screen or pad or any suitable input device. In some embodiments, input devices 635 may be an input port. For example, an input port (e.g., a network interface card (NIC), a USB port or a wireless port or card) may be used to receive images from image recorder 650, in-vivo device 100, or an external storage. It will be recognized that any suitable number of input devices may be operatively connected to computing system 610 as shown by block 635. Output devices 640 may include one or more displays, speakers and/or any other suitable output devices. It will be recognized that any suitable number of output devices may be operatively connected to computing system 610 as shown by block 640. Any applicable input/output (I/O) devices may be connected to computing system 610 as shown by blocks 635 and 640. For example, a network interface card (NIC), a printer or facsimile machine, a universal serial bus (USB) device or external hard drive may be included in input devices 635 and/or output devices 640.

Computing system 610 may be operatively connected to for example a monitor 660 and a point and click device 665. According to embodiments of invention, images obtained by in-vivo device 100 and provided to computing system 610 may be displayed on monitor 660. Point and click device 665, that may be a mouse as known in the art may be used by a user in order to indicate objects or regions of interest, e.g., as described with respect to FIG. 4.

As shown, a tissue model 626, an optical model 627 and an illumination model 628 may be loaded into memory 624 (other or different models may be used). Tissue model 626, optical model 627 and illumination model 628 may be any suitable code or data. In some embodiments, a tissue model may include an optical model, an illumination model and/or other models. It will be understood that the tissue model, optical model and illumination model discussed herein may be implemented by any applicable construct or module and may be combined or broken into components as known in the art. For example, in one embodiment, these models may be a data structure that may enable an application to search for distance values based on a set of imaging parameters. In other embodiments, tissue model 626, optical model 627 and illumination model 628 may include parameters that may be used by an application in order to derive, determine or estimate a distance as described herein. For example, an application (e.g., executable code 625) may extract an intensity and color from a pixel in an image, may modify such values based on data in illumination model 628 and/or optical model 627 and may use such modified values as input to tissue model 626 in order to estimate a distance of an object represented by the pixel. For example, illumination model 628 may dictate that a level or percentage of red color extracted from a pixel is to be modified by a factor of 1.03. For example, based on information related to the light source used by in-vivo device 100 when the relevant image was obtained it may be necessary to perform such modification prior to estimating a distance using tissue model 626.

In another case, based on information or parameters related to lenses or mirrors used when acquiring an image, optical model 627 may dictate that an intensity of light associated with the pixel is to be reduced by a factor of 0.98. For example, if tissue model 626 was designed to provide an estimation of distance based on a specific light intensity of light source 120, when using a different, (e.g., weaker) light source, an adaptation may be required in order to produce adequate results. In yet another embodiment, tissue model 626, optical model 627 and/or illumination model 628 may be an executable code. For example, optical model 627 and/or illumination model 628 may be an executable code that may be provided with input in the form of a color and intensity and may provide output in the form of modified values of color and intensity as described herein. Likewise, tissue model 626 may be an executable code that may receive a set of imaging parameters, e.g., a color and intensity (possible as modified by models 627 and 628) and may return as output a distance estimation. It will be understood that FIG. 1B shows an exemplary schematic illustration of an in-vivo imaging system and that other embodiments or implementations are possible. For example, some or all of tissue model 626, optical model 627 and illumination model 628 may be implemented in hardware (e.g., by an application-specific integrated circuit (ASIC) or a chip) or they may be implemented in firmware, e.g., in order to increase speed of operation.

Accordingly and as described herein, embodiments of the invention may include an article such as a computer or processor readable medium, or a computer or processor storage medium, such as for example a memory, a disk drive, or a USB flash memory, encoding, including or storing instructions, e.g., computer-executable instructions, which when executed by a processor or controller, carry out methods disclosed herein. For example, a system may include a storage medium such as memory 624, computer-executable instructions such as executable code 625 and a controller such as controller 605. Some embodiments may be provided in a computer program product that may include a machine-readable medium, stored thereon instructions, which may be used to program a computer, or other programmable devices, to perform methods as disclosed above.

Other embodiments of the invention may be or may include a system for estimating a distance, size or other dimension of an object imaged by an in-vivo imaging system. The system may include a workstation or any other suitable computing device comprising a memory and a processor. The memory may be configured to store an image captured by an in-vivo imaging system, and the processor may be configured to select at least one pixel in the image, where the pixel is associated with the imaged object. The memory may store a tissue model, an optical model and an illumination model. The processor may be configured to calculate, based on a tissue model (and/or an optical model and/or an illumination model) and data associated with the pixel, a distance parameter related to a distance of the object from the in-vivo imaging system, wherein the tissue model is designed to provide at least one mapping of at least one imaging parameter to at least one distance parameter. For example, the processor to select a pixel, calculate a distance parameter related to a distance of the object from the in-vivo imaging system or calculate a size or other dimension of the object may be controller 651 or controller 605 or it may be included in computing system 130 or computing system 610. In some embodiments the task of estimating a size, distance or other dimensions or parameters related to an object captured or imaged by an imaging system or device such as in-vivo imaging device 100 may be distributed among a number of controllers, processors or computing systems. For example, computing system 130 and controllers 605 and 651 may jointly perform any computational tasks or calculations in order to estimate a distance and/or size of an object as described herein. As described herein, computing system 130 and controllers 605 and 651 may communicate or exchange (e.g., over wireless or wired links) any data, parameters or information. Computing system 130 and controllers 605 and 651 may collaborate efforts and computational resources in performing any relevant tasks or methods described herein.

According to an embodiment of the invention, a tissue model may be generated, obtained and/or provided and used as described herein. Various aspects, traits or qualities of a tissue as related to, reflected in, or represented by a digital image of the tissue may be measured, determined, derived or modeled. As known in the art, a pixel in a digital image may be associated with imaging parameters, values or levels of, e.g., hue, intensity, color, brightness, luminance, chromaticity, saturation levels of such imaging parameters or any other relevant data, parameters or values. Such imaging parameters as related to a tissue or object may be affected by various aspects. In particular, such imaging parameters may be affected by the distance of the object from the imaging device used for acquiring the image. Accordingly, a tissue model may associate, correlate or map one or more imaging parameters, e.g., as reflected by data associated with pixels, to a distance.

A tissue model may be designed and generated such that it may be suitable for use with any patient and/or any tissue. In other embodiments, a model may be specifically generated or adapted to a specific tissue, patient, patient condition or other relevant aspects. For example, it may be empirically or otherwise determined that tissues in the colon exhibit specific attributes, behavior, response or other aspects or traits related to light and/or imaging. Accordingly, a model may be generated in accordance with such attributes or aspects such that the model may be used in order to process images of colon tissues as described herein. For example, a model generated based on known levels or constants of absorption or reflection of light by a tissue, color and intensity of light emitted from a tissue and possibly, parameters related to a relevant system and environment, may be used to determine or estimate a distance of a tissue segment from the imaging device. In some embodiments, data extracted from pixels in a digital image may be related to a model in order to calculate a distance and/or size of an object or region.

A tissue model may be designed to be specifically adapted or suitable for specific cases, patients, patient condition or illness etc. For example, a first model may be suitable for young children and a second model may be specifically suitable or adapted for old patients. A model may be related to a condition of a patient. For example, a first model may be used for a patient who was on a normal diet when the images taken while a second model may be used for a patient who was made to abstain from food for twenty four hours, or made to drink a large amount of liquids prior to the images being taken. In some embodiments, a base or universal model may be modified according to relevant aspects. For example, a base or universal model may be modified based on the imaging system used or aspects related to the light used, e.g., intensity or color composition of light emitted by light source 120. In yet other embodiments, a tissue model may be specific to a region or anatomical organ in a body.

For example, a tissue model may be generated for the colon or gastrointestinal (GI) tract. A tissue model may represent or exhibit attributes of real tissue as reflected in a digital image. A tissue model may likewise symbolize, describe, stand for, contain, or be based on, imaging parameters of a real tissue. For example, an interaction of a tissue with light may be known, e.g., spectral characteristics of a given light that is made to be reflected from the tissue may be studied or determined and represented by a tissue model. Likewise, an amount or percentage of light reflected from a tissue, or imaging parameters related to the intensity, per color intensity, hue, luminance, chromaticity or brightness of light reflected and/or absorbed by a tissue may be studied, determined and/or known. For example, by examining a series of images obtained using known relevant parameters such as any relevant parameters related to the light used, the tissue being imaged, the distance of the tissue from the imaging device and the optical and illumination aspects or characteristics, a model of the tissue may be generated or constructed. In some embodiments, an image may be analyzed, various aspects may be determined, and a tissue model may be selected or generated dynamically and/or automatically.

A tissue model may include a mapping of imaging or other parameters to a distance or other relevant parameters. Accordingly, a tissue model may be used to map, correlate or associate one or more imaging or other parameters, values or other data in an image to a distance or a size. For example, given relevant parameters related to light reflected from a tissue as described herein are known and the relevant optical and illumination aspects or characteristics are known, a color and/or intensity of a tissue segment or an object as reflected by an image may be mapped to a distance of the tissue segment or object from the imaging system used for obtaining the image.

Various combinations of parameters that may be extracted from, or computed based on, an image may be likewise mapped. For example, a level of absorption or reflection of only part of the light spectrum may be examined and/or mapped as described herein. In one particular embodiment, a tissue model may analyze only red light reflected from a tissue. Red light may be light detected only in a red color channel of an imager, where each of the red, blue and green color channels detects light in a wide range of wavelengths centered about wavelengths in the red, blue and green color ranges, respectively. In one example, the red color range includes light having wavelengths in a range of 600-750 nanometers (nm). A tissue model may map the intensity of light reflected from a tissue (e.g., the colon) and detected by the red channel (or red pixel sensors) of the imager, to a distance. For example, assuming light traveling through a medium is attenuated according to a reciprocal relation or function of distance, a distance of an object may be determined by the equation: $D=A+B/\sqrt{R}$, where D is the distance of the object from the imaging device at the time the image was acquired, A and B are constants selected as described herein and R is the intensity of red light.

In generating a tissue model, any method of mapping, associating or correlating one or more imaging parameters such as an intensity or color of light to a distance may be used. For example, using an image in which the distance of objects from the imaging system is known, a human may manually map colors of a known tissue to distance to generate a tissue model (the use of the tissue model, as discussed herein, is automated). In other embodiments, extrapolation, adaptation, image analysis or other methods or techniques may be used in order to automatically map various parameters in an image to a distance such that a mapping, association or correlation of imaging parameters to distance is realized.

Figure 2:
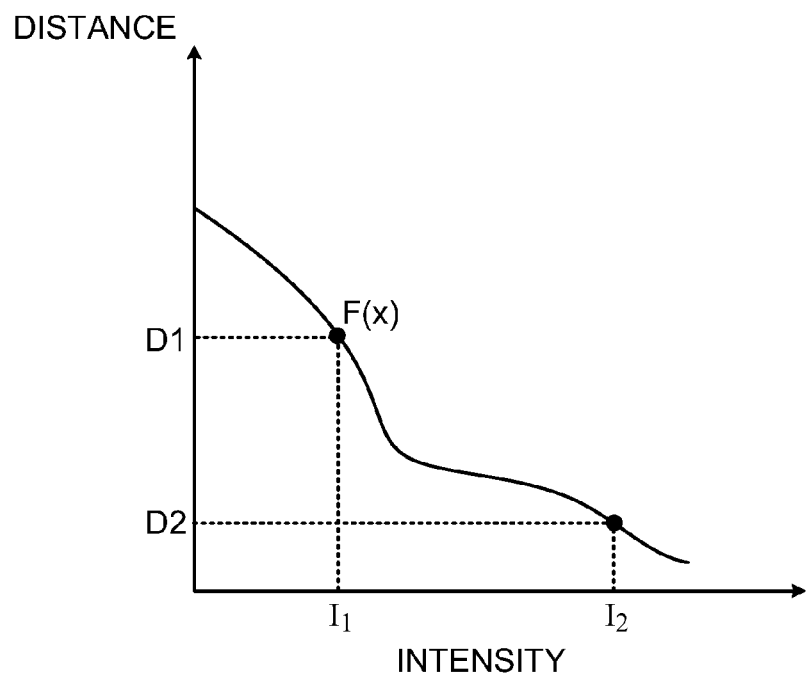
FIG. 2 shows a schematic distance versus intensity graph according to embodiments of the present invention.

Reference is now made to FIG. 2, which shows an example of a simplified distance versus intensity plot or graph that may be calculated according to one embodiment of the present invention. Although conceptually, the graph shown in FIG. 2 may be the tissue model, it will be understood that the graph shown in FIG. 2 is produced for an illustrative purpose in order to visually represent information or a mapping that may be included and/or provided by a tissue model. It will be understood that a typical tissue model may include complex mapping calculations typically related to a number of parameters. For example, a tissue model may map a number of parameters' values (e.g., a specific intensity value and a specific color value or saturation) to a distance. A model may include any applicable computations. For example, a tissue model may include factors that may be applied to values determined by a graph or table, rules (e.g., upper or lower limits) etc. As shown, the intensity level $I_1$ corresponding to a distance of an object from the imaging device $D_1$ is lower than intensity $I_2$ corresponding to a distance $D_2$ where $D_1 > D_2$. Although a decrease of intensity with increased distance may be known and intuitive, the rate of decrease, its curve, and its relationship to specific distances may be specific to the tissue, the imaging system, the environment and various parameters related to the light as described herein. Furthermore, the decrease may not necessarily be constant or linear but may, as shown, exhibit non linear behavior that may too, be related to the tissue and optical or other aspects. The function F(x) may be derived based on empirical or other data and may be used, e.g., by a tissue model or be included as part of a tissue model in order to quickly map any intensity level to a distance. Accordingly, an automated procedure may map, associate or correlate any point, region or object in an image upon being provided with an intensity of the object (e.g., as indicated or represented by relevant pixels). Such automated procedure may use F(x) in order to perform such mapping. Thus, once the distance function F(x) has been derived, the distance of any point in an image from the imaging system can be inferred or estimated from the function.

Although a highly simplified graph of a distance to intensity relation is shown in FIG. 2, it will be understood that any relation may likewise be derived or mapped. For example, an intensity of a specific light wavelength or color (e.g., red) may be similarly computed and graphed. The red color channel may be modeled alone, primarily or with greater weight than other color channels, for example, since it may be more robust to variability in the turbid media. Furthermore, a relation of distance (or size) to a number of parameters or aspects may be generated. For example, a tissue model that may be or may include a mapping that takes into account both an intensity and color may be generated such that both intensity and color are used in order to determine or estimate a distance or size of an object by the tissue model. In some embodiments, a large number of imaging parameters may be used in order to map imaging parameters to a distance. Any computations or calculations, e.g., applying coefficients or factors to selected parameters or results may be performed and/or be part of a tissue model described herein.

According to embodiments of the invention, a tissue model, an optical model and/or an illumination model may be used in order to process an image. Each of these models may be used alone or in combination which each other model, for example, to correct images to account for the features being modeled.

Figure 6:
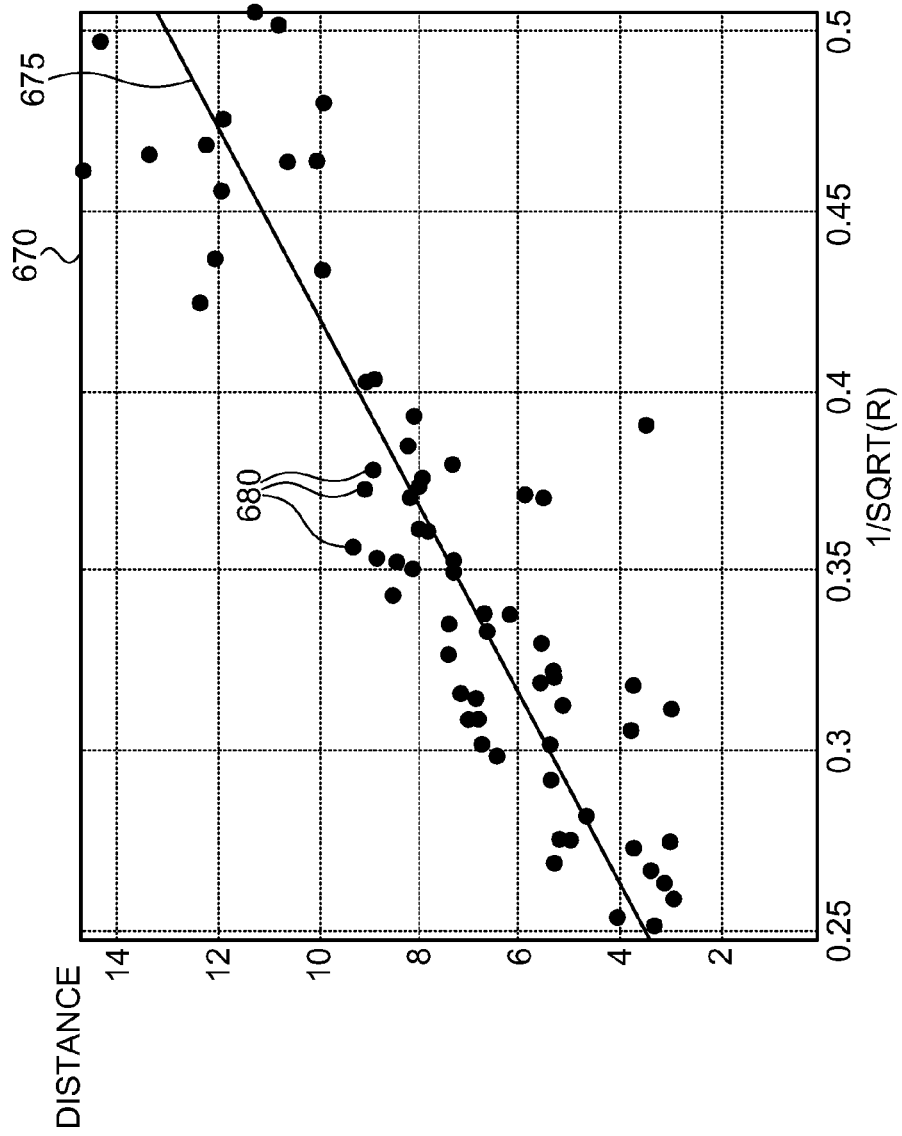
FIG. 6 shows measured intensity of red light with respect to distance and a modeling graph according to embodiments of the present invention.

Reference is now made to FIG. 6 which shows a plot of red light intensity as a function of distance. More specifically, a relation of an inverse of a square root of red light intensity $(1/\sqrt{R})$ to distance is shown where the distance is measured from the imaging device to the imaged object. According to embodiments of the invention, actual measured values 680 may be used to compute curve 675 which may be used to map an intensity of red light to distance. Based on actual measurements and a computed curve as shown in FIG. 6, a tissue model may be generated. Any other applicable measurements and curves or mapping may be similarly made and generated, e.g., other colors, brightness, luminance, chromaticity or saturation of colors may be measured and a respective curve may be computed. Accordingly, any measured parameters may be used to compute a curve similar to the one shown by 675. A tissue model may be generated based on any number of measured parameters and/or computed curves or mapping as described herein. For example, a tissue model may be based on a number of curves, graphs or functions related to a respective number of parameters such as brightness, luminance and chromaticity. Various methods, functions or other means may be employed in order to combine any number of such graphs or functions such that given a pixel in an image, the distance of the object or region associated with such pixel may be determined.

Figure 7:
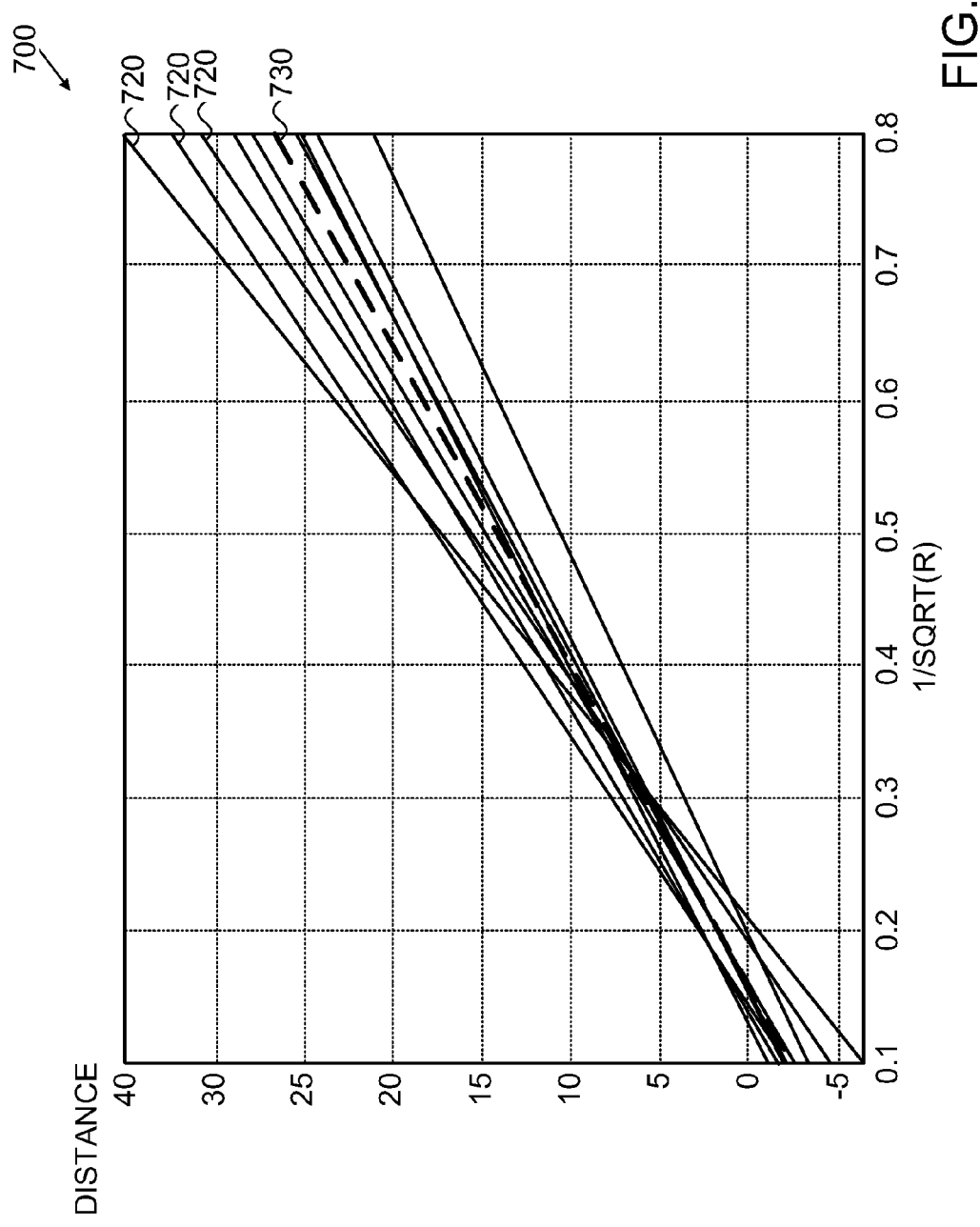
FIG. 7 shows a plurality of curves illustrating a relation of red light to distance according to embodiments of the present invention.

A tissue model may be generated based on measurements obtained from any number of tissues. For example, images of a specific tissue or region (e.g., the colon) from a plurality of patients may be used to produce a plurality of plots and curves as shown by FIG. 6. Such plurality of curves may then be used to derive a curve that may be used in a tissue model suitable for most of the patients. For example, a universal tissue model may be generated based on an average, estimation or other representation of a plurality of plots, curves or models related to a plurality of patients. Reference is now made to FIG. 7 showing a plurality of curves 720 which may be similar to curve 675 described herein. Curves 720 may be generated based on measurements obtained from a plurality of patients. Curve 730 may be derived by computing an average, a weighted average, a mean, a midrange, a median or any other suitable value or function associated with curves 720. Accordingly, a curve that may be suitable for use with most patients may be derived. Likewise, based on such and other curves, mapping and other information as described herein, a tissue model (that may be referred to herein as a universal tissue model) that may be used with, or suitable for, any patient may be generated.

According to embodiments of the invention, an optical model may be used in order to process and/or analyze an image. An optical model as referred to herein may be or may be generated based on distortion in the image. For example, light acquired by an imaging system may travel through a medium (e.g., a dome or window in in-vivo device 100) and may bend non-uniformly through the medium due to optical variations therein. An optical model may include parameters or coefficients related to magnification distortion, radial distortion, or other types of distortion, for example, to account for and correct such distortion in the images. For example, an optical model may include reflection, refraction, diffraction or other optical distortion coefficients or parameters. Lenses or mirrors used by an imaging device may cause specific distortion effects throughout all the images the device captures. Additionally, distortion effects may be introduced as a result of the design, shape and other aspects of viewing window 160, as well as the medium through which light travels when exiting device 100. Such aspects may be accounted for in an optical model and may, accordingly, affect a mapping of imaging parameters to a distance.

An optical model may take any such aspects into account and may be used in order to correctly or better map imaging parameters to a distance as described herein. For example, an optical model may be used in order to derive one or more constants or coefficients that may be used to adjust a base tissue model to a specific environment or circumstance. For example, a first optical model may be generated for a first in-vivo device 100 having a specific imaging system, viewing window and light source and a second optical model may be generated for a second in-vivo device 100 having a different imaging system, viewing window and/or light source. Accordingly, a base tissue model may be adapted to a specific circumstance or device based on an optical model. In other cases and as described herein, an optical model may be used to modify imaging parameters or values, e.g., prior to using a tissue model in order to estimate a distance as described herein. In some embodiments, calibration or configuration parameters of the imaging system and/or environment may be used in order to derive an optical model. For example, a direction of light source 120 with relation to imaging system 110 or the type and number of lenses or mirrors used by imaging system 110 may be observed when generating an optical model. Accordingly, an optical model may represent any optics related aspects of the equipment and environment relevant to an acquisition of images by an in-vivo device and may thus be use in order to correctly map imaging parameters to a distance as described herein.

Reference is made to FIG. 8 which shows a graph that may be or may be used to generate an optical model. As shown by image 820, an image of a sphere may be distorted. For example, due to various optical aspects or parameters related to lenses used, magnification in an acquired image may not be even or constant and may vary, e.g., as a function of the distance from the center of the image (or the distance from another reference point). Accordingly, a plot of a relative magnification as a function of distance from the center of the image may be produced as shown by 810. Such plot (or a related function) may be used in order to correct an image, e.g., eliminate magnification distortions as seen in image 820. For example, the plot shown by 810 may be used to derive a function that alters a magnification based on a distance from the center of the image. The function may be generated or derived such that it eliminates the deficiencies shown by plot 810. For example, the function may determine that based on a distance from the center of the image, the number of pixels per unit area is to be reduced or increased by a respective number or ratio. The function of the optical model may be the same for all imaging devices or may be calibrated specifically for each device, for example, using few programmable parameters. The function may be calibrated, for example, by comparing one or more images or image features captured by the device to one or more pre-stored reference images. Calibrating parameters for each device may eliminate or reduce inter-capsule variations in the optics and illumination models to get more accurate distance measurement.

For example, in correlation with plot 810, a function may reduce the size of regions at a distance of 60 pixels from the center of the image (where, as shown, a substantial magnification may be exhibited) and increase the size of regions at a distance of 120 pixels from the center of the image (where, as shown, a distortion related to a reduced size is seen). As shown by image 830, by applying a suitable function that manipulates a magnification based on a distance from the center of an image, distortions caused by uneven or otherwise varying magnification may be removed. An optical model may comprise any functions, mappings or other parameters designed to compensate for any undesirable optical effects that may be included in an image. For example, as described herein, a size of a region or object may be calculated based on the number of associated pixels. However, optical distortions such as those depicted by image 820 may cause wrong estimations or calculations. Accordingly, by reducing or increasing a size or areas thus eliminating undesirable optical effects, e.g., by removing or adding pixels, an image may be made suitable for size estimation based on a number of pixels. Any other optical aspects may be accounted for in an optical model used to process or analyze an image in order to derive size or other dimensions estimations.

An illumination model may represent any relevant illumination parameters or aspects related to an acquisition of an image. An illumination model may include, but is not limited to, the level or intensity of illumination or luminance emitted (e.g., by a light source such as light source 120) and/or absorbed or reflected (e.g., by a medium and/or tissue). For example, an illumination model may define aspects related to parameters such as color intensity, hue, color saturation, luminance, chromaticity, brightness of light may be used in order to compile, generate, produce or obtain an illumination model. For example, such parameters related to an environment in which images are acquired, e.g., the medium through which light travels before being captured by an imaging device may be used in generating an illumination model. Likewise, parameters related to an irradiation or light source, e.g., the wavelength and/or intensity of light being emitted by a light source may be known and accounted for in an illumination model. A light source may be fitted with lenses, mirrors or various diffractive or other optic elements. Accordingly, an illumination model may be generated such that any relevant effect of such lenses or elements is taken into account. An illumination model may be based on, or in accordance with, illumination sources, lenses and other components, their respective usage, type and attributes or any other parameters that may be pertinent to illuminating or imaging tissues or objects.

In other embodiments, an illumination model may be based on the specific device or system used for acquiring the relevant image. For example, the central point in an image may be illuminated more brightly than points located near the edge of the image. Such difference in illumination level or other parameters may result from the shape or other characteristics of the illumination sources, their location in a device etc. In some embodiments, an illumination model may remove such differences, calculate calibrating parameters or otherwise take any such optical, illumination or other aspects into account. The calibrated parameters of the illumination model may be the same for all (or all of a set, model or series) imaging devices or may be calibrated specifically for each device, for example, using programmable parameters. An illumination model that describes illumination differences or inhomogeneity may be defined with respect to a reference geometry or plane. For example, the reference geometry may be a sphere at radii $r1 \ldots rN$ centered about the imaging device. In some embodiments, the optimal illumination model may vary as the distance varies between the imaged object and the illumination source or imaging device. Some embodiments may use an average or most often optimal illumination model or may iteratively select and switch to the optimal illumination model for each image or image stream segment.

Figure 9:
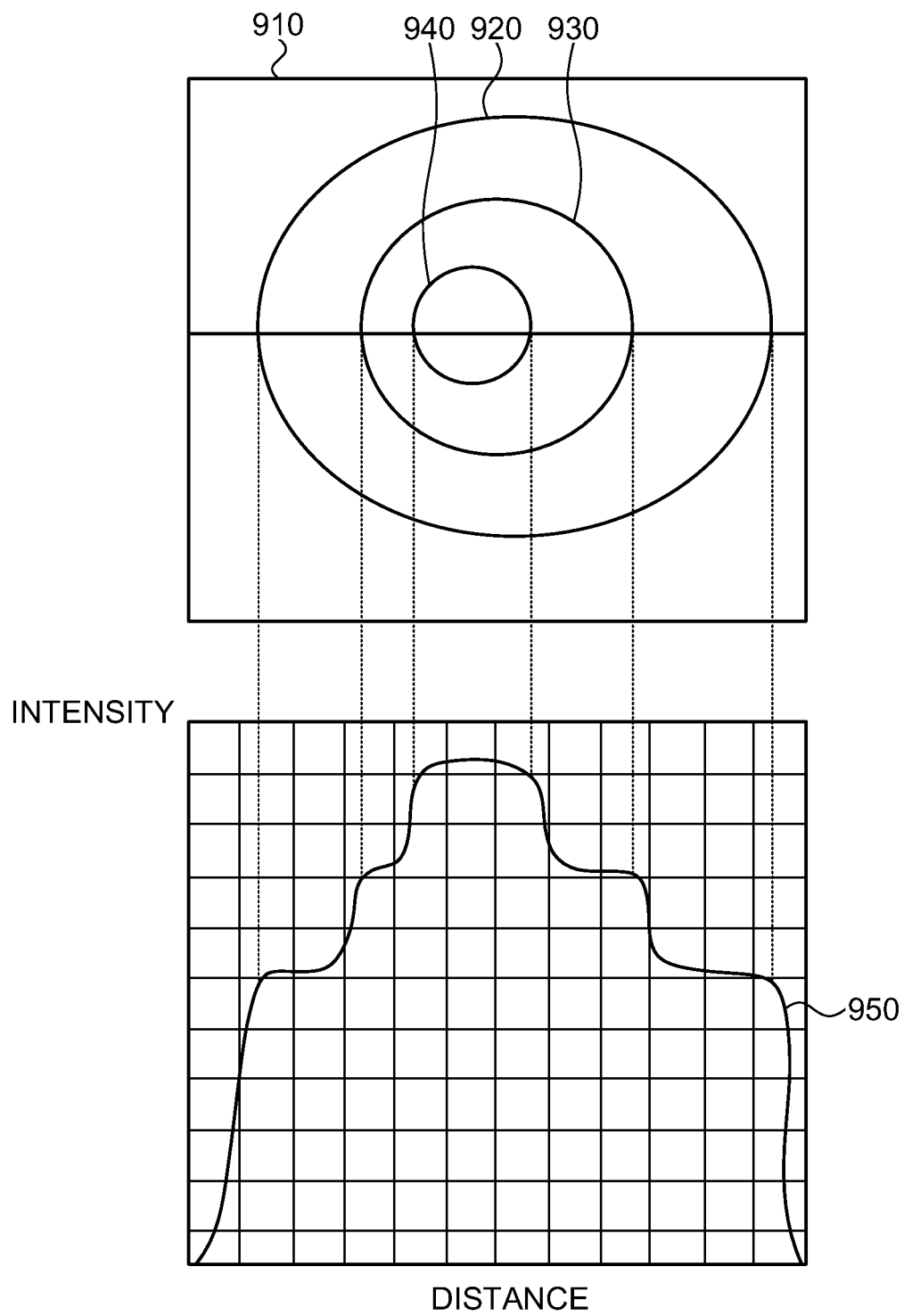
FIG. 9 is a graph modeling an illumination parameter according to embodiments of the present invention.

Reference is made to FIG. 9 which graphically illustrates an exemplary component of an illumination model according to embodiments of the invention. As shown by 910, light emitted by a light source (e.g., light source 120) may be distributed unevenly in space. Such phenomena may be due to characteristics of the light source, obstacles and/or the medium through which light travels. For example, the shape of viewing window or dome 160 may cause light to be distributed unevenly in space. As shown, three regions 920, 930 and 940 associated with different light intensities may be created by a light source. For example, region 940 may be a region where the highest light intensity is observed, region 930 may be a region where lower intensity is seen and region 920 may be a region associated with the lowest light intensity. As shown by a function 950, light distribution as a function of distance (e.g., from the center of the image) may be modeled by a graph. Such graph or a function associated with such graph may be used as an illumination model or part thereof. An image may first be input into an illumination model to correct the uneven illumination in the image. Once the illumination is corrected, the image output from the illumination model may then be input into the tissue model to output distance computations. For example, using function 950 or a related function, the intensity of one or more pixels may be modified such that the uneven distribution of light is compensated for, or otherwise accounted for. Accordingly, after compensating for the specific distribution, the distance between the one or more pixels from the center of the image (or other reference point) may be analyzed and used as described herein. It will be understood that FIG. 9 is a simplified example used for explanatory purpose and that embodiments of the invention may employ far more sophisticated graphs and models. In particular, FIG. 9 illustrates a model related to a single (intensity) parameter, however, embodiments of the invention may utilize models that incorporate any number of parameters. In one example, similarly to modeling a light distribution, a number of light colors (e.g., red, green and blue) may be modeled separately and/or other illumination parameters such as hue, intensity, color, brightness, luminance, chromaticity may be modeled. Accordingly, an illumination model may be a combination of any number of models of any number of illumination parameters or aspects. In device with a plurality of (e.g., 4) illuminating sources (e.g., LEDs), the parameters may be the intensity and/or the direction of each illuminating source. In another example, an optics module may be used for size calculations in order to obtain corrected (e.g., XY) coordinates that along with distance coordinates (e.g., Z) calculated with the tissue model may create 3D points in (XYZ) space.

Although in one embodiment, illumination and optical models may be used in conjunction with a tissue model and/or in order to generate or use a tissue model, it will be understood that such embodiment is one of a number of possible embodiments. Accordingly, parameters such as an illumination (e.g., measured in units of candela per square meter (cd/m2), lux (cd·sr/m2) or watt per square meter (W/m2)) may be incorporated in a tissue model through an illumination model or otherwise. Likewise, the levels or relative levels of red, green and blue or specific wavelengths in a light used as described and/or emitted from a tissue may be detected, calculated or otherwise derived and used in a generation of a tissue model as described herein.

According to some embodiments and/or in some cases, a size of an object or a region may be estimated or determined based on the number of pixels associated with the object or region. For example, a distance of a tissue represented by a set of pixels may be determined by employing a tissue model as described herein. As known in the art, using a pixel resolution of an imaging device and a distance of an imaged object, at least the size of the visible (in the image) part of the object may be derived. For example, in a specific imaging system, the number of pixels required to represent an area of 20×20 micron at a distance of 500 micron may be 10. Accordingly, in a simple case where substantially all pixels in an area of interest are associated with similar imaging data, e.g., the same color and intensity, it may be assumed that the distance of the area of interest from the imaging device is known. Accordingly and as described herein, by employing imaging parameters related to the imaging system, e.g., a pixel resolution, the size of the area or object may be determined or estimated. Similarly, a length of a line (e.g., drawn by a user on an image) may be determined and indicated or displayed. For example, a physician may use a mouse or other point and click device to draw a line across a region in an image and be provided with the length of such line. Accordingly, by drawing a line across a region the physician may quickly be provided with an estimation of the region's size.

Figure 3:
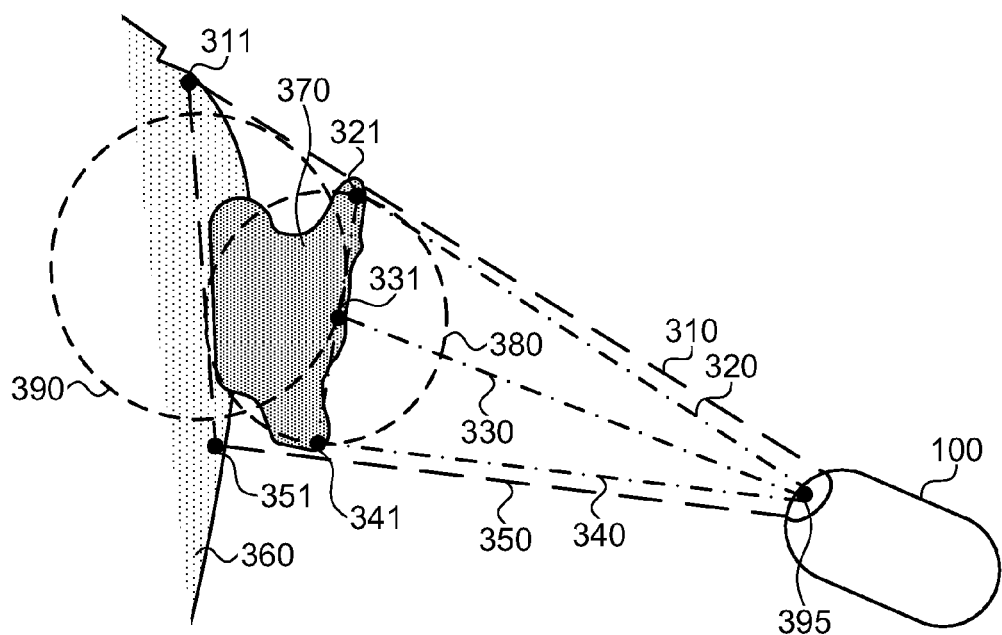
FIG. 3 shows exemplary points and geometrical shapes defined in an image according to one embodiment of the present invention.

Reference is now made to FIG. 3, which illustrates a method of determining or estimating a size of an in-vivo object according to embodiments of the invention. It will be understood that although FIG. 3 provides a schematic, two dimensional illustration, embodiments of the invention are not limited in this regard and, in fact, may be applicable to three dimensional (3D) shapes or objects. It will further be understood that FIG. 3 is a simplified illustration, produced for explanatory purposes. As shown in FIG. 3, an image of a tissue 360 and of an object 370 (that may be for example a polyp, a lesion, a tumor, a cyst, a choristoma, a hamartoma, a tissue malformation or nodule or any other pathology or malignancy) may be acquired by imaging device 100.

By determining a location or position of an object in an image, e.g., with respect to a reference point such as imaging system 110 and further determining a distance of such object from the reference point, an object's location in a three dimensional space may be defined and/or determined. In some embodiments, three dimensional (e.g., X, Y, Z values in a cartesian coordinate system) coordinates of selected pixels in the image may be determined. As further shown, a number of distances from the imaging device of a respective number of locations may be determined. For example and as shown, five distances 310, 320, 330, 340 and 350 of respective five points or locations 311, 321, 331, 341 and 351 may be determined. Based on distances calculated as described herein, a number of geometrical shapes may be derived. For example, the triangle defined by points or locations 395, 311 and 351, the triangle defined by points or locations 395, 321 and 341 and circles (or spheres in the 3D case) 380 and 390 may all be calculated, computed, derived or otherwise obtained such that their location, orientation, position, size, volume and/or any relevant parameters are known. Based on determining such geometrical shapes and their relevant attributes, a size of an object may be determined or estimated according to a geometrical relation. For example, a geometrical relation may be the confinement of object 370 by circle 380, the confinement circle 380 by the triangle with vertices at points 395, 311 and 351, the intersection area of circles 380 and 390 etc.

For example, the size of an object may be determined or estimated based on the object being enclosed, surrounded, contained or otherwise related to one or more geometrical shapes, structures or objects. For example, the size of object 370 may be determined or estimated based on it being wholly or partially enclosed by triangles, circles or spheres described herein.

In some embodiments, an input from a user may be received. For example, a physician using system 600 may indicate an object of interest and/or may further indicate a specific region or reference. For example, a physician observing an image of tissue 360 and object 370 may draw a line connecting locations 321 and 341 thus indicating that the size of object 370 is to be computed or estimated or the length of the drawn line is to be estimated or determined. In other embodiments, an object may be automatically identified, e.g., based on various attributes such as color, hue or reflected light intensity that may be different from respective attributes of the surrounding environment, e.g., nearby tissue.

In some embodiments, predefined methods, constraints, parameters or algorithms may be used in order to select or determine locations or points such as points 311, 321, 331, 341 and 351. Reference is additionally made to FIG. 4, which illustrates a method of selecting points in an image according to embodiments of the invention. The image in FIG. 4 may be presented to a user, for example on monitor 660. For example and as shown, points around and/or on object 370 (shown from a top view) may be determined. Such points or locations may represent or define lines from point 395 (that may be an imager shutter or other point or component in an imaging device installed on device 100) shown in FIG. 3 to such points. For example, distance lines 310, 320, 330, 340 and 350 may be derived by first defining points 311, 321, 331, 341 and 351 and further connecting such points to point 395.

In some embodiments, selecting points as described herein may be based on an input from a user. For example, a user may draw (e.g., using a suitable graphic application and a point and click device) arrow or other indicator 410 from point 415 to point 420 on object 370. For example, a physician may thus indicate that the size of object 370 is to be calculated, determined or estimated. According to embodiments of the invention, the center of point 311 may be determined to be a pixel that is located a predefined number of pixels from point 420, in the direction of arrow 410. For example, the center of point 311 may be selected to be a pixel that is seven pixels from point 420 in a direction defined by arrow 410. Likewise, the center of point 321 may be seven or other number of pixels from point 420 in the opposite direction along arrow 410. In some embodiments, point or location 331 may be selected to be the middle of arrow 410 and the center of points 341 and 351 may be determined in a way similar to the way or method used for determining points 311 and 321. In another embodiment, arrow 410 may be initially marked by a user or physician and may then be automatically refined by an algorithm.

According to some embodiments of the invention, a size of points such as points 311, 321, 331, 341 and 351 may be predefined or dynamically defined. For example, a circle having a radius of five pixels around a center of a point may define the point. For example, point 311 may be defined by a center point or pixel determined as described herein and any pixel within five pixel distance from such center pixel or point. According to embodiments of the invention, after or during determining the pixels included in, or defining a point such as point 311, such pixels may be analyzed, examined and/or verified.

For example, various attributes or parameters of tissue 360 and/or object 370 may be determined and a pixel verification process may determine whether a selected point represents or is associated with tissue 360 and/or object 370. Determining a selected point is associated with a tissue may comprise relating various imaging parameters associated with the pixel to imaging parameters associated with the tissue. For example, a ratio of green light to blue light reflected from tissue 360 and/or object 370 may be determined, e.g., by identifying tissue 360 and further deriving an average ratio. Alternatively, a tissue model described herein may be used to determine levels, ratios or values of a tissue. Accordingly, pixels in point 311 and/or 351 (which may be expected to represent points or locations on tissue 360) may be analyzed in order to determine whether they include such green to blue ratio. According to some embodiments, if a predefined number of pixels selected as described herein in order to define a point comply with a determined attribute of the relevant tissue or object then the relevant pixels may be marked as acceptable and may further be used to define the point. Alternatively, if a predefined number of pixels in a candidate point fail to meet a criterion such as a ratio of colors, level of intensity or any other criteria that may be predefined, e.g., by a tissue model described herein, or dynamically, by dynamically calculating various parameters or criteria for a specific image, tissue or object, then that point may not be selected or used.

According to some embodiments, upon determining that less than a required number of pixels comply with a criteria as described herein, an alternative point may be defined and the process of validating pixels may be repeated. For example, if a predefined number of pixels around the center of point 311 are determined to fail a criteria as described herein, an alternative location of point 311 may be attempted. For example, if an insufficient number of pixels around point 311 is found as described herein, the center of point 311 may be automatically redefined, e.g., by computing system 610, by selecting a pixel that is twelve (rather than seven) pixels from point 420 and the process of validating pixels around such newly selected center may be repeated. Alternatively, rather than examining pixels at a distance of five pixels from a selected center pixel, upon determining a failure to meet a criteria e.g., determining that pixels in a point do not represent a background tissue or an object as expected, a larger number of pixels may be observed. For example, rather than examining pixels at a distance of five pixels from a selected center, all pixels at a distance of seven pixels from such center may be examined as described.

According to embodiments of the invention, a distance from selected and/or defined points to a common reference point may be determined. For example, the distances from points 311, 321, 331, 341 and 351 to point 395 may be determined. By analyzing an image, embodiments of the invention may determine an actual or estimated distance of an object or region from the imaging device, namely, the distance between the imaging device and the object at the time the image was acquired. More specifically, the distance represented by each pixel in an image may be determined. For example, a grayness level, illumination intensity, color range, hue and/or saturation parameters associated with a pixel may be observed and, using a tissue model described herein, such observed parameters or values may be mapped, associated, correlated or translated to a distance parameter.

According to embodiments of the invention, a tissue model, an optical model, an illumination model or any relevant combination of such models may be associated with an image. As described herein, a model may map one or more parameters or a combination of parameters, e.g., a light intensity or color to a distance. According to embodiments of the invention, a pixel in an image may be associated with a number of attributes, values or parameters. Accordingly, by examining one or more values or parameters associated with a pixel, e.g., the associated intensity or color and relating such values to a tissue model, the distance represented by such pixel may be determined, calculated or otherwise derived. For example and as described herein, parameters or values such as an intensity and/or color may be mapped to a distance by a model. Accordingly, by performing such mapping of pixels in an image to a respective distance, the distances 310, 320, 330, 340 and 350 of respective points 311, 321, 331, 341 and 351 from point 395 may be determined.

Returning now back to FIG. 3 and as shown, based on defined points in space and distances between such points, various geometric shapes may be automatically defined or determined, e.g., by computing system 610, and their size or other attributes may likewise be determined. For example, various geometric shapes may be defined by some or all points 311, 321, 331, 341, 351 and 395 and relevant distances. For example, polygons and/or circles on a two dimensional plane, or cubes, spheres or other volumes in a three dimensional space may be defined by such points and distances. For example, a triangle having corners or vertices at points 395, 321 and 341 may be defined. Provided with the distances from point 395 to points 321 and 341 and further provided with the angle between their respective directions from point 395, the above triangle may be defined. Accordingly, the distance between points 321 and 341 may be derived and known using known in the art geometric tools, methods or calculations. The distance between points 321 and 341 may be of great interest to a user. For example, a physician interested to be provided with a size estimation of object 370 may mark points 321 and 341 on object 370 and be provided with the size or length of the line connecting points 321 and 341 thus being provided with a size estimation of object 370.

By determining and/or defining geometric shapes related to an image, for example, using a location (e.g., distance and direction from an imaging device) of points, locations, objects or regions as reflected by the image, embodiments of the invention may perform various other size or volume estimations or determinations. For example, a circle 380 confined by the triangle defined by points 321, 341 and 395 may be determined using known geometric tools or calculations. Likewise, a circle 390 confined by a triangle with corners or vertices at points 311, 351 and 395 may be determined. According to some embodiments of the invention, the area defined by the intersections of circles 380 and 390 may be used in order to estimate or determined the size of object 370.

Various constants, factors or coefficients may be applied, e.g., to geometrical dimensions determined as described herein, to values extracted from or associated with, pixels etc. For example, a predefined factor, e.g., 1.17 or 0.87, that may be applied to the intersection area may be used to estimate the size of object 370. Although a two dimensional (2D) example is described herein, it will be understood that estimating volumes or planes in a three dimensional (3D) space may be performed in a similar way. For example, a cone in a three dimensional space may be defined similarly to the way a triangle may be defined as described herein, likewise, a sphere or cube confined by such cone may be determined. Accordingly, a determined volume of such defined geometrical shapes may be used to estimate a volume or size of an object, e.g., a polyp confined by, or otherwise related to, such determined volumes.

According to embodiments of the invention, various constants, factors, coefficients or values may be used when estimating or determining a size or volume of an object. For example, factors "A" and "B" in the equation $D=A+B/\sqrt{R}$ as discussed above. In addition or in other cases or embodiments, factors may be applied to distances or other measures calculated as described herein with respect to FIG. 3. For example, a computed or derived distance between points 311 and 351 may be subject to a factor of 0.93 and a calculated or determined distance between points 321 and 341 may be subject to a factor of 1.04. Such factors may be determined or derived based on experiments or other empirical information. In other embodiments, such factors may be based on, or part of, the tissue model used, a determined level of deviation of the image or tissue from the tissue model used, metadata related to the patient or subject etc.

Reference is now made to FIG. 5, showing a flowchart describing a method of determining a size of in-vivo objects according to embodiments of the invention. As shown by block 510, the flow may include obtaining an image of a tissue of an anatomical organ acquired by an imaging device. For example, device 100 may obtain images while traveling through a patient's digestive system, e.g., the stomach, large or small intestines.

As shown by the dashed line of block 515, the flow may include presenting the image to a user and receiving an input from the user indicating a region of interest and/or an object. For example, a user may indicate a region or area of interest by dragging an on screen indicator (using a mouse or other pointing device) around an in-vivo object presented in the image, or by selecting a central point in boundaries of the object, or by another input method, for example marking the object using a touch screen, defining a line or arrow across or along a region or object in the image. It will be understood that an object as referred to herein may be any definable object in an image. In particular, an object may be a tissue segment. An object may be a polyp, a lesion, a tumor, a cyst, a choristoma, a hamartoma, a tissue malformation or nodule or any other pathology or malignancy. In other embodiments, a user may, for example, choose two points on a display (e.g., using a mouse) possibly corresponding to edges of an object, thus indicating an object or area of interest. Any other methods of generating and/or receiving a user indication of an object may be used without departing from the scope of the invention.

Alternatively or additionally, defining a region of interest or object may be performed automatically. For example, an article such as a controller, computing device, data processor or other unit may detect an object of interest, for example a suspected pathology using computer image analysis techniques. For example, using a tissue model as described herein, regions, tissues or objects which may not be part of a predefined tissue type (e.g., as defined by the tissue model) may be identified and possibly marked. For example, using various image processing techniques, tissues deviating by a predefined level from an expected tissue or a predefined tissue model may be identified, marked (e.g., circled) and may further be selected for further processing as described herein. In one example described in reference to FIG. 4, object 370 may be automatically defined or indicated, for example, by arrow 410. Object 370 and/or arrow 410 may be generated fully automatically by a computing device or semi-automatically, for example, first by a user generating an initial object and arrow and then computing device automatically refining the object and arrow.

Various other constraints or configuration parameters may be applied in an automatic identification and/or selection of regions, tissues or objects. For example, based on a configured or other rule, criteria or parameter, only objects larger than a predefined size may be identified or selected. Such an embodiment may be desirable, for example where pathologies such as polyps of a first size range (e.g., 0.5 mm to 1.5 mm) may be diagnosed differently from pathologies or polyp of a second, larger size range (e.g., 1 cm-3 cm). Accordingly, embodiments of the invention may be configured to detect, identify and/or select objects or suspected tissues having a predefined size.

Other attributes of detected or selected objects, regions or tissue segments may be applicable. For example, similarly to modeling a tissue as described herein, a pathology may be modeled. For example, an interaction of a tissue with a known pathology (e.g., a polyp, lesion, tumor or cyst) with light may be known, e.g., spectral characteristics of a given light that is made to be reflected from a pathological tissue may be studied or determined and represented by a pathology model.

In some embodiments, an amount or percentage of light reflected from the pathology, or parameters related to the intensity, per color intensity, hue, luminance, chromaticity or brightness reflected from the pathology may be determined. Accordingly, by relating a tissue in an image to such pathology model it may be determined whether the tissue is associated with the pathology. Accordingly, objects or tissue regions may be automatically identified, indicated or marked and/or selected for further processing based on their relation to a pathology.

As shown by block 520, the flow may include selecting one or more points in the image related to a region of interest and/or an object. As described herein, points on and around an object or region may be selected such that one or more geometric relations may be calculated, defined and/or determined. For example, points may be selected such that a specific triangle or cone which confines, or is otherwise related to, the region or object, is defined.

As shown by block 525, the flow may include determining whether or not the selected points are acceptable. For example, points associated with the surrounding tissue may be designated as acceptable or proper. As described herein, various verification or validation processes, algorithms or other means may be used in order to determine that selected points are associated with a tissue or are otherwise acceptable. For example, by relating attributes or data associated with pixels representing a region or object in an image to a tissue model or to calculated averages values in an image, a group of pixels representing a point in an image may be verified, validated or designated as acceptable. Various constraints, criteria or rules may be applied in order to define or validate a point. For example, a point may only be accepted if a minimum, predefined number of acceptable pixels are associated with the point.

As shown by block 530, the flow may include determining the distances of the selected points from the imaging device using a tissue model and illumination model. For example, a universal or specific tissue model may be used to map a number of parameters to a distance. For example, information that may be extracted from pixels in an image, e.g., brightness, color, hue or saturation of light may be mapped by a tissue model to a distance of objects represented by such pixels from the imaging device. As described herein, a model may define the set of parameters used for mapping, various manipulations that may be applied to such parameters and/or any related calculations or computations. For example, a specific color may be observed or ignored when processing image data extracted from pixels, a predefined coefficient or constant may be used to modify values and various relations or dependencies between values or parameters may be applied. Accordingly, any combination of parameters or values, e.g. color intensity, hue, luminance, chromaticity or brightness, may be used to determine a distance. Likewise, any processing, calculation or computation may be applied to such values or parameters in order to determine a distance of objects from an imaging device.

As shown by block 535, the flow may include defining a geometrical relation based on the location of the selected points and their respective distances from the imaging device using the optics model to correct the optics distortion. For example, the triangle having vertices at points 395, 311 and 351 may be defined based on the location of points 311 and 351 with respect to point 395 (which may be a reference point, e.g., a center of a dome of device 100, a center of a lens of imaging system 110 etc.). The triangle may be further defined by the distances of points 311 and 351 from point 395 where these distances may be computed as described herein. A geometrical relation defined may be the relation of the triangle described herein with circle 380 shown in FIG. 1A and/or with object 370. For example, the geometrical relation may be a confinement of circle 380 by the triangle described herein. Another geometrical relation may be the confinement of object 370 in the triangle. Such geometrical constraints or relations may enable an estimation of a size as described herein.

As shown by block 540, the flow may include calculating a size estimation related to the region of interest and/or object based on the geometrical relation. For example, having defined the triangle with vertices at points 311, 351 and 395 and circles 380 and 390 as shown in FIG. 1A and further defining or determining their inter relations, a size estimation of object 370 which is confined as shown may be determined or calculated. Any estimations may be made based on the relations of geometrical shapes. For example, in one embodiment, the size of object 370 may be estimated by the area where circles 380 and 390 intersect. In other embodiments, a volume of intersections of spheres that may be defined similarly to the way circles 380 and 390 are defined may be used for producing a size estimation. It will be understood that having defined geometrical shapes or objects and their relation to an object in an image as described herein, any applicable calculations may be used in order to derive a size estimation of an object, e.g., using any known in the art methods and calculations. As shown by block 545, the flow may include providing the size estimation. For example, the size estimation may be displayed on a computer display screen, e.g., overlaid on an image, possibly located on the object of interest. Other embodiments may print the size estimation, send it over a network or store the size estimation as known in the art.

It may be appreciated that the size of image objects may be estimated in a post-processing stage, after image frames are captured and transmitted and/or in "real-time" during frame capture and transmission.

It may be appreciated that an image or frame may be a digital or analog representation of real-life objects and that reference to objects in the frame may refer to the visual representation of those objects. For example, the size of objects in an image may refer to a region of pixels in the image that visually represent a real-life object.

It is noted that while embodiments of the invention described herein are adapted for imaging of the GI tract, the devices and methods disclosed herein may be adapted for imaging other body cavities or spaces.

Different embodiments are disclosed herein. Features of certain embodiments may be combined with features of other embodiments; thus certain embodiments may be combinations of features of multiple embodiments.

Embodiments of the invention may include an article such as a computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method of estimating a distance of an object captured by an in-vivo imaging system, the method comprising:
   obtaining, by said in-vivo imaging system, an image of said object;
   selecting at least one pixel in said image, said at least one pixel associated with said object; and
   calculating, based on a tissue model and data associated with said at least one pixel, a distance parameter related to a distance of said object from said in-vivo imaging system, the tissue model selected from the group consisting of: a universal tissue model suitable for a plurality of patients; a tissue model specific to a patient condition; and a tissue model specific to a region of the GI tract, wherein said tissue model includes a representation of an interaction of tissue with light.

2. The method of claim 1, comprising:
   selecting at least two pixels in said image, said at least two pixels associated with said object; and
   calculating a size parameter related to said object by relating a sum related to said at least two pixels to an imaging parameter related to said in-vivo imaging system.

3. The method of claim 1, comprising:
   selecting at least two pixels in said image, said at least two pixels associated with respective at least two locations in a space captured by said image;
   determining, based on said tissue model and data associated with said at least two pixels, at least two distance parameters respectively related to a distance of said at least two locations from said in-vivo imaging system;
   determining a geometrical relation of said at least two locations and said at least two distance parameters to said object; and
   calculating, based at least in part on said geometrical relation, a size parameter of said object.

4. The method of claim 3, wherein said geometrical relation is determined based on a geometrical shape and wherein said geometrical shape is selected from the group consisting of: a two dimensional geometric shape and a three dimensional geometric shape.

5. The method of claim 3, wherein said geometrical shape is selected from the group consisting of: a triangle, a circle, a cone, a sphere and a cube.

6. The method of claim 3, comprising displaying said size parameter and said distance parameter on a display screen.

7. The method of claim 1, comprising calculating said distance parameter based on an illumination model.

8. The method of claim 1, wherein said tissue model provides a mapping of an intensity of light associated with said at least one pixel to at least one distance parameter, and wherein said mapping is a mapping of the intensity of light detected by only a red color channel to the at least one distance parameter.

9. The method of claim 1, comprising calibrating said tissue model to specific parameters of said in-vivo imaging system.

10. The method of claim 1, wherein said object is selected from the group consisting of: a polyp, a lesion, a tumor, a cyst, a choristoma, a hamartoma, a tissue malformation and a nodule.

11. A system for estimating a distance of an object imaged by an in-vivo imaging system, the system comprising:
    a workstation comprising a memory and a processor, the memory to store an image captured by an in-vivo imaging system, and the processor to:
    select at least one pixel in said image, said at least one pixel associated with said object; and
    calculate, based on a tissue model stored in the memory and data associated with said at least one pixel, a distance parameter related to a distance of said object from said in-vivo imaging system, the tissue model selected from the group consisting of: a universal tissue model suitable for a plurality of patients; a tissue model specific to a patient condition; and a tissue model specific to a region of the GI tract, wherein said tissue model includes a representation of an interaction of tissue with light.

12. The system of claim 11, wherein said processor is to:
    select at least two pixels in said image, said at least two pixels associated with said object; and
    calculate a size parameter related to said object by relating a sum related to said at least two pixels to an imaging parameter related to said in-vivo imaging system.

13. The system of claim 11, wherein said processor is to:
    select at least two pixels in said image, said at least two pixels associated with respective at least two locations in a space captured by said image;
    determine, based on said tissue model and data associated with said at least two pixels, at least two distance parameters respectively related to a distance of said at least two locations from said in-vivo imaging system;
    determine a geometrical relation of said at least two locations and said at least two distance parameters to said object; and
    calculate, based at least in part on said geometrical relation, a size parameter of said object.

14. The system of claim 13, wherein said processor is to determine said geometrical relation based on a geometrical shape and select said geometrical shape from the group consisting of: a two dimensional geometric shape and a three dimensional geometric shape.

15. The system of claim 13, wherein said processor is to select said geometrical shape from the group consisting of: a triangle, a circle, a cone, a sphere and a cube.

16. The system of claim 13, comprising a display screen, wherein said processor is to display said size parameter and said distance parameter on the display screen.

17. The system of claim 11, wherein said processor is to calculate said distance parameter based on an illumination model.

18. The system of claim 11, wherein said in-vivo imaging system is a swallowable capsule.

19. The system of claim 11, wherein said processor is to calibrate said tissue model to the specific parameters of said in-vivo imaging system.

20. The method of claim 8, comprising modifying the mapping provided by the tissue model by an illumination model based on illumination used to capture the image.

21. A method of estimating a distance of an object captured by an in-vivo imaging system, the method comprising:

obtaining, by said in-vivo imaging system, an image of said object;

selecting at least one pixel in said image, said at least one pixel associated with said object; and calculating, based on a tissue model and data associated with said at least one pixel, a distance parameter related to a distance of said object from said in-vivo imaging system, the tissue model selected from the group consisting of: a universal tissue model suitable for a plurality of patients; a tissue model specific to a patient condition; and a tissue model specific to a region of the GI tract, wherein said tissue model includes a representation of an interaction of tissue with light, and wherein said tissue model provides a mapping of at least one of: a color associated with said at least one pixel to at least one distance parameter, and an intensity of light associated with said at least one pixel to at least one distance parameter, and wherein the tissue model is adjustable based on an imaging environment.

22. The method of claim 21, wherein the imaging environment includes at least one of: a condition of a patient, an imaging system used, the light used for imaging, and anatomical organ in a body.

23. The method of claim 1, wherein said tissue model provides a mapping of at least one of: a color associated with said at least one pixel to at least one distance parameter, and an intensity of light associated with said at least one pixel to at least one distance parameter, and wherein each color is modeled separately.

* * * * *